US007993657B2

(12) United States Patent
Gennaro

(10) Patent No.: US 7,993,657 B2
(45) Date of Patent: Aug. 9, 2011

(54) ANTIBODY PROFILES CHARACTERISTIC OF TUBERCULOSIS STATE

(75) Inventor: Maria Laura Gennaro, New York, NY (US)

(73) Assignee: University of Medicine and Dentistry of New Jersey, Newark, NJ (US)

( * ) Notice: Subject to any disclaimer, the term of this patent is extended or adjusted under 35 U.S.C. 154(b) by 0 days.

(21) Appl. No.: 11/494,140

(22) Filed: Jul. 26, 2006

(65) Prior Publication Data

US 2007/0026473 A1 Feb. 1, 2007

Related U.S. Application Data

(60) Provisional application No. 60/702,757, filed on Jul. 26, 2005.

(51) Int. Cl.
*A61K 39/04* (2006.01)
*A61K 39/02* (2006.01)
*G01N 33/53* (2006.01)

(52) U.S. Cl. ............... 424/248.1; 424/184.1; 424/185.1; 424/234.1; 435/4; 435/7.1; 435/7.2; 435/29; 530/300; 530/350

(58) Field of Classification Search ............... 424/184.1, 424/185.1, 234.1, 248.1; 435/4, 7.1, 7.2, 435/29; 530/300, 350
See application file for complete search history.

(56) References Cited

U.S. PATENT DOCUMENTS

| 4,016,043 | A | 4/1977 | Schuurs et al. |
| 6,087,163 | A | 7/2000 | Gennaro et al. |
| 6,506,384 | B1 | 1/2003 | Zolla-Pazner et al. |
| 6,596,281 | B1 | 7/2003 | Gennaro et al. |
| 2003/0143652 | A1* | 7/2003 | Simonson ..................... 435/7.32 |
| 2005/0089904 | A1 | 4/2005 | Beaulieu et al. |

FOREIGN PATENT DOCUMENTS

| WO | 0011214 | 3/2000 |
| WO | PCT/US00/12197 | 11/2000 |
| WO | PCT/US00/12257 | 11/2000 |
| WO | 0179274 | 10/2001 |
| WO | WO2005/080990 | 9/2005 |

OTHER PUBLICATIONS

Cole, S.T, et al, Nature, vol. 396, Nov. 12, 1998, pp. 190-198.*
Cole, S.T., et al, Nature, vol. 393, Jun. 11, 1998, pp. 537-543.*
Mustafa, A.S., Molecular Immunology, vol. 39, pp. 113-119, 2002.*
American Thoracic Society, Diagnostic Standards and Classification of Tuberculosis in Adults and Children. Am. J. Respir. Crit. Care Med. 161:1376-95. 2000.
Bifani, P.J. et al., Global Dissemination of the *Mycobacterium tuberculosis* W-Beijing Family Strains. Trends Microbiol. 10:45-52. 2002.
Bothamley, G.H., Serological Diagnosis of Tuberculosis. Eur. Respir. J. 8, suppl. 20:676s-688s. 1995.
Bothamley, G.H. et al., Specificity of Antibodies and Tuberculin Response After Occupational Exposure to Tuberculosis. J. Infect. Dis. 166:182-6. 1992.
Colangeli, R. et al., Three-step purification of lipopolysaccharide-free, polyhistidine-tagged recombinant antigens of *Mycobacterium tuberculosis*. J. Chromatogr. B. 714:223-235. 1998.
Grzybowksi, S. et al., Reactivation in inactive pulmonary tuberculosis. Am. Rev. Resp. Dis. 93:352-360. 1966.
Grzybowski, S. et al., Tuberculosis among patients with various radiologic abnormalities, followed by the chest clinic service. Am. Rev. Resp. Dis. 104:605-608. 1971.
Harboe, M. The 38-kDa protein of *Mycobacterium tuberculosis*: a review. J. Infect. Dis. 166:874-884. 1992.
Harth, G. Glutamine synthetase of *Mycobacterium tuberculosis*: extracellular release and characterization of its enzymatic activity. Proc. Natl. Acad. Sci. U.S.A. 91:9342-6. 1994.
Honer Zu Bentrup, K. and D.G. Russell, Mycobacterial persistence: adaptation to a changing environment. Trends Microbiol 9:597-605. 2001.
Hutter, B. and M. Singh, Properties of the 40 kDa antigen of *Mycobacterium tuberculosis*, a functional L-alanine dehydrogenase. Biochem. J. 343 Pt 3:669-72. 1999.
Kaplan, M.H. and M.W. Chase, Antibodies to mycobacteria in human tuberculosis. I. Development of antibodies before and after antimicrobial therapy. J. Infect. Dis. 142:825-34. 1980.
Manca, C.L. et al., *Mycobacterium tuberculosis* CDC1551 induces a more vigorous host response in vivo and in vitro, but is not more virulent than other clinical isolates. J. Immunol. 162:6740-6. 1999.
McKinney, J.D. et al., Persistence of *Mycobacterium tuberculosis* in macrophages and mice requires the glyoxylate shunt enzyme isocitrate lyase. Nature 406:735-8. 2000.
Monack, D.M. et al., Persistent bacterial infections: the interface of the pathogen and the host immune system. Nat. Rev. Microbiol. 2:747-65. 2004.
Nolan, C. and E. Am, Tuberculosis in a cohort of Southeast Asian refugees. Am. Rev. Resp. Dis. 137:805-809. 1988.
Segal, W., Growth dynamics of in vivo and in vitro grown mycobacterial pathogens, p. 547-573, In G.P. Kubica and L. G. Wayne (ed.), The Mycobacteria. A Sourcebook. Marcel Dekker, Inc., New York. 1984.
Sherman, D.R. et al., Regulation of the *Mycobacterium tuberculosis* hypoxic repsonse gene encoding alpha-crystallin. Proc. Natl. Acad. Sci. U.S.A. 98:7534-9. 2001.
Shi, L. et al., Expression of Th1-mediated immunity in mouse lungs induces a *Mycobacterium tuberculosis* transcription pattern characteristic of nonreplicating persistence. Proc. Natl. Acad. Sci. U.S.A. 100:241-6. 2003.
Shi, L. et al., Effect of growth state on transcription levels of genes encoding major secreted antigens of *Mycobacterium tuberculosis* in mouse lung. Infect. Immun. 72:2420-2424. 2004.
Intentionally omitted.
Sorensen, A.L. et al., Purification and characterization of a low-molecular-mass T-cell antigen secreted by *Mycobacterium tuberculosis*. Infect. Immun. 63: 1710-1717. 1995.

(Continued)

Primary Examiner — Rodney P. Swartz
(74) Attorney, Agent, or Firm — Lowenstein Sandler PC

(57) ABSTRACT

Serum antibody assays capable of distinguishing cases of inactive TB from cases of active TB include a combination of at least three *M. tuberculosis* protein antigens, at least one for which a positive response is consistent with inactive TB and at least one for which a negative response is consistent with inactive TB. Preferred assays further distinguish other TB classes. Also, antigen kits for performing such assays.

6 Claims, No Drawings

OTHER PUBLICATIONS

Stewart, G.R. et al., Tuberculosis: a problem with persistence. Nat. Rev. Microbiol. 1:97-105. 2003.

Turneer, M. et al., Humoral immune response in human tuberculosis: immunoglobulins G, A, and M directed against the purified P32 protein antigen of *Mycobacterium bovis* bacillum Calmette-Guerin. J. Clin. Microbiol. 26: 1714-9. 1988.

Voskuil, M.I. et al., Inhibition of respiration by nitric oxide induces a *Mycobacterium tuberculosis* dormancy program. J. Exp. Med. 198:705-13. 2003.

Wayne, L.G., Dormancy of *Mycobacterium tuberculosis* and latency of disease. Eur. J. Clin. Microbiol. Infect. Dis. 13:908-14. 1994.

Weber, I. et al., Anaerobic nitrate reductase (narGHJI) activity of *Mycobacterium bovis* BCG in vitro and its contribution to virulence in immunodeficient mice. Mol. Microbiol. 35:1017-25. 2000.

Wilkins, E.G.L., The serodiagnosis of tuberculosis, p. 367-380, in P.D.O. Davies (ed.), Clinical tuberculosis. Chapman and Hall Medical, London. 1994.

Wilkinson, R.J. et al., Human T- and B-cell reactivity to the 16kDa alpha-crystallin protein of *Mycobacterium tuberculosis*. Scand. J. Immunol. 48:403-9. 1998.

Zhang, Y. et al., Genetic analysis of superoxide dismutase, the 23 kilodalton antigen of *Mycobacterium tuberculosis*. Mol. Microbiol. 5:381-391. 1991.

Zuber, P. et al., Long-term risk of tuberculosis among foreign-born persons in the United States. JAMA 278:304-307. 1997.

Cole, S.T., et al., "Deciphering the Biology of *Mycobacterium tuberculosis* from the Complete Genome Sequence," Nature, vol. 393, Jun. 11, 1998, p. 537-544.

Cole, S.T., et al., "Deciphering the Biology of *Mycobacterium tuberculosis* from the Complete Genome Sequence," Nature, vol. 396, Nov. 12, 1998.

Extended European Search Report dated Mar. 3, 2010, received in connection with EP Application No. 06788711.7.

A. Davidow et al, "Antibody profiles characteristic of *Mycobacterium tuberculosis* infection state," Infection and Immunity, vol. 73, No. 10, pp. 6846-6851 (Oct. 2005).

D. Vincenti et al., "Identification of early secretory antigen target-6 epitopes for the immunodiagnosis of active tuberculosis," Molecular Medicine, vol. 9, No. 3/4, pp. 105-111 (Mar./Apr. 2003).

Silva et al., "Factors associates with humoral response to ESAT-6, 38 kDa and 15 kDa in patients with a spectrum of tuberculosis", Int. J. Tuberc. Lung Dis, 7(5):478-484 (2003).

\* cited by examiner

ANTIBODY PROFILES CHARACTERISTIC OF TUBERCULOSIS STATE

This application claims the benefit of prior U.S. provisional application 60/702,757, filed Jul. 26, 2005.

TECHNICAL FIELD

This invention relates to assays for *Mycobacterium tuberculosis* (*M. tuberculosis*).

BACKGROUND

Diagnosis for the disease tuberculosis (TB) traditionally includes a combination of clinical, bacteriological and radiographic evidence, typically culture and smear tests, the tuberculin skin test (TST) and chest x-ray.

Antibodies specific for a number of proteins expressed by *M. tuberculosis* are detectable in human serum. Antibody assays are speedy and relatively inexpensive, and thus are a potentially valuable diagnostic and screening technique. There are several diagnostic categories for TB: active disease, inactive (past) TB, and two categories characterized by the absence of radiographic chest abnormality: latent infection and infection-free. Detection of active TB is, of course, clinically important. Detection of inactive TB is clinically significant, because persons with inactive TB are more than an order of magnitude more likely to develop active TB than are persons who have latent TB. Distinguishing active TB from inactive TB is significant from a public-health standpoint, as it permits concentration of resources, which are often very limited in countries most severely impacted by TB, where the danger is greatest. Distinguishing inactive TB from states characterized by normal chest x-rays is similarly important from a public-health standpoint.

Attempts to utilize detection of serum antibodies to diagnose a TB state have focused on finding an antigen or antigens whose binding correlates positively with that particular state, for example, antigens for whom positive ELISA results signal active TB. Diagnosis of TB states by antibody serum tests has suffered from lack of accuracy.

An aspect of this invention is assays for detection of human serum antibodies with improved ability to predict TB states accurately, particularly to discriminate between active TB and inactive TB.

Another aspect of this invention is reagent kits containing *M. tuberculosis* proteins as antigens for such antibody assays.

SUMMARY

TB states include five recognized classes. Class 1 (sometimes denominated Class 0-1) indicates absence of infection. In this application we refer to that state as "infection-free". Class 2 is latent infection. The foregoing two classes both are characterized by the absence of radiographic chest abnormality, which we sometimes refer to as "chest x-ray normal" or, for short, "CXR-normal." Class 3 is active TB. Class 4 is inactive TB. Class 5 is TB suspected, diagnosis pending. This five-class system was adopted by the board of directors of the American Thoracic Society in July 1999, in a joint statement with the U.S. Centers for Disease Control (CDC) titled "Targeted Tuberculin Testing and Treatment of Latent Tuberculosis Infection." The classification has been endorsed by the Council of the Infectious Diseases Society of America. See Am. J. Respir. Crit. Care Med. (April 2000) 164 (4 pt 2): S221-47. Class 4, inactive TB, as defined is "Tuberculosis; not clinically active. This classification is defined by a history of previous episode(s) of tuberculosis or abnormal stable radiographic findings in a person with a positive reaction to tuberculin skin test, negative bacteriologic studies (if done), and no clinical and/or radiographic evidence of current disease. Persons in Class 4 may never have received chemotherapy, may be receiving treatment for latent infection, or may have completed a previously prescribed course of chemotherapy."

This invention is human serum antibody assays for TB with improved ability to distinguish inactive TB from active TB as compared to known single-antibody assays and, preferably also from latent TB and infection-free categories. Assays according to this invention are based on and utilize the well-known antigen-antibody reaction. The type of protocol, that is, sandwich assay or competitive assay, is not critical. I utilize an ELISA (enzyme-linked immunosorbent assay) that is a sandwich format including as a first reagent immobilized antigen and as second reagent a labeled anti-antibody that binds to antibodies immobilized by the first reagent. However, other formats for detection of serum antibodies can be used. See, for example, U.S. Pat. Nos. Re. 3,654,090, 3,791,932, 3,850,752, 3,839,153, and 3,879,262.

Assays of this invention utilize proteins of *M. tuberculosis* as reagents, either as antigen first reagent to immobilize serum antibodies or as antigen labeled reagents, or both. Assays of this invention are characterized by the use of at least 3 antigens; and by the inclusion of antigens of at least two types: first, at least one antigen that is specific for an antibody whose presence is an indicator of inactive TB relative to active TB and, second, at least one antigen that is specific for an antibody whose absence is an indicator of inactive TB relative to active TB. When utilized in my preferred sandwich assay, a positive response from an antigen or antigens of the first type coupled with a negative response (that is, absence of a positive response) from an antigen or antigens of the second type is indicative of inactive TB as distinguished from active TB. Certain preferred assays include one or more antigens of a third type whose positive response is an indicator of active TB or inactive TB, or both, as distinguished from latent TB or infection-free. Antigens of the first type in some instances are antigens of the third type, although antigens of the third type need to be antigens of the first type. Similarly, antigens of the second type may in some instances be antigens of the third type.

Assays according to this invention include performing separate reactions in separate locations or containers, for example, separate spots on a card or stick surface or separate wells of microtitre plates. In such a format, use of a color-forming label such as horseradish peroxidase is possible, as one can tell which antigen or antigens lead to a positive response, namely color. Assays according to this invention also include performing separate reactions commonly in separate locations of a single array, such as occurs when antigen first reagents are immobilized at identifiable, separate locations on the surface of an array, and the entire array is exposed to serum, washed, exposed to common second reagent, washed again, and read. In this approach the second reagent is labeled with a signaling label, for example, a fluorescent moiety or a radioactive isotope, so that positive results at individual locations of various first-reagent antigens can be detected.

Preferred assays according to this invention are constructed so as to have two results, positive result or negative result, for each antigen. For the type of sandwich ELISA I have used and that is described in this application, one establishes the division point (cut-off point) between positive and negative and adjusts antigen concentration or other conditions in the assay so that only results above cut-off give a positive result. This can be illustrated by reference to Table 3. In Table 3, for AlaDH antigen, the median results were: for cases of active TB, 0.199; for cases of inactive TB, 0.140; and for cases that were CXR-normal, 0.106. In designing an assay the concentration of the antigen can be adjusted to provide the desired cut-off, that is, so that only cases of active TB will produce sufficient color to be judged "positive." All other cases will give insufficient (or no) color and be judged "negative" in the assay. Therefore, the AlaDH antigen result, if positive, will be consistent with active TB but not inactive TB, and it will also be consistent with active TB but not a CXR-normal class. However, a positive or negative result will not distinguish inactive TB from CXR-normal classes, because results for all of them would be negative. In this application, including the claims, such positive results are considered to signify serological recognition by an antigen. Looking at the medians for ESAT-6 and 16 kDa, one can see that a properly adjusted concentration for the cut-off will mean that a positive result is consistent with inactive TB but inconsistent with both active TB and CXR-normal classes. In this case a negative result will not distinguish active TB from CXR-normal classes.

For a result to be considered positive, each first-reagent antigen must lead to the appropriate signal. For example, for an assay to be considered indicative of inactive TB, of the antigens listed in Table 4, those with an odds ratio (OR) greater than 1 must give a "high" signal and those with an OR below 1 must give a Low signal (in the case of 38 kDa Ag a low or Medium signal); and of the antigens listed in Table 5, all must give a "High" signal to distinguish inactive TB from a CXR-normal state.

To improve confidence in results, one can include more antigens, utilize antigens whose OR differs from 1.0 more greatly, utilize a different alpha value or a combination of two or more of the foregoing.

To develop an assay according to this invention, one can start with a group of characterized serum samples and a putative set of antigens, and obtain data such as is shown in Table 3. For subsets or for all the antigens, one then performs a statistical analysis, for example, the analysis discussed in connection with Tables 4 and 5. To bring another antigen ("antigen X") into the mix without having to generate Table 3 data for antigens already tested, one simply saves the serum samples originally used and tests antigen X against them. With only that extra testing a new set or new subsets can be analyzed statistically to produce expanded Tables 4 and 5. Evaluation of another protein of M. tuberculosis for inclusion in assays of this invention can be accomplished routinely according to the assay and data-analysis procedures set forth herein. The procedures include measuring serum levels of antibodies according to the ELISA described herein, expressed conventionally as "optical density" or absorbance (as $OD_{450}$), to obtain data such as reported in Table 3, wherein differences are considered significant only at $p<0.05$ with and without controlling for multiple comparisons using the Bonferroni approach; estimating multivariate logistic regression models using only those antigens identified as statistically significant; and using backward elimination so that the odds ratios associated with each and every antigen are statistically significant (CI not including 1.0) using one model or the other as shown in Table 4.

Described below in the Examples is work with an initial panel of eight antigens. While the results are impressive with this panel, no attempt has yet been made to optimize our assay procedure by changing the panel. However, many TB antigens are known. From reported work with sera from mice, primates and humans utilizing other TB antigens, I have identified several candidates for evaluation in kits and assays according to this invention. These include Rv0440, Rv3881c and Rv2195 (Havlir, D. V. et al (1991) Infect. Immun. 59, 665-670); Lodes, M. J. et al (2001) J Clin Microbiol 39, 2485-2493); Rv2495c, Rv2195, Rv2700 and Rv3763 (Bothamley (2003) Lancet 361, 2082); (Bothamley, G. H. (2004) Clin Diagn Lab Immunol 11, 942-951); and Rv1837c and Rv3803c (Singh, K. K. et al. (2005) Clin Diagn Lab Immunol 12, 354-358).

The experimental work reported in this application was with serum from a special and particularly difficult population of persons. Most active TB cases were negative when tested for bacterium in sputum smear. Correctly diagnosing such individuals by chest x-ray is quite difficult and requires subjective judgment of a highly skilled physician. For this group of active cases, individual antigens are quite inefficient at identifying active cases in a population that includes inactive and CXR-normal classes of TB. As shown in Table 6 and described below, individual antigens indicated the active cases correctly only 6-15% of the time. The assay of this invention, including a panel that includes both antigens that positively correlate to inactive TB and antigens that negatively correlate to inactive TB, did threefold better, as much as 43% of the time.

This improvement is practically significant. If used for checking immigrants, for example, nearly half of the active TB cases that would otherwise not be detected would be detected, even using the unoptimized antigen panel initially tested.

This invention also includes assay kits comprising multiple M. tuberculosis antigens as first, immobilizing reagent or as second, labeled reagent, or both. Preferred kits include multiple M. tuberculosis antigens as first reagent and anti-human IgG antibodies as labeled second reagents.

The details of one or more embodiments of the invention are set forth in the accompanying drawings and the description below. Other features, objects, and advantages of the invention will be apparent from the description and drawings, and from the claims.

DETAILED DESCRIPTION

Known strategies for serum antibody assays for TB are characterized by a strategy of looking for positive responses from one or more than one M. tuberculosis protein antigens, whereas the present invention looks for negative responses as well to distinguish inactive TB from active TB and, preferably, also from CXR-normal classes.

Included below as part of this application is a report of experimental work and statistical analysis performed under my direction. The report presents data and analysis that support and describe aspects of this invention. It describes work utilizing eight different known TB proteins as antigens utilizing samples of sera from a clinically evaluated population of 353 human subjects.

Based on the analyses of assay results (shown in Table 3), models were designed to distinguish one TB state from another by calculating an odds ratio ("OR") and confidence interval ("CI") that the result was indicative of one state as opposed to another state. Three analytical models were used for logistic regression. The models differed in the alpha value utilized. Alpha values were selected according to the Bonferroni criterion. Two models were used to distinguish inactive TB from active TB: model 1, based on results for a given antigen that are significant at alpha equal to 0.003; and model 2, based on results for a given antigen that are significant at alpha equal to 0.05. One model was used to distinguish inactive TB from chest x-ray normal: model 3, based on results for a given antigen that are significant at alpha equal to 0.003. (The alpha value of 0.003 is obtained by dividing 0.05 by 16, which is the product of the numbers of antigens in the panel (8) times the states to be distinguished (2 in all cases)).

Referring to Table 4, the analysis presents an odds ratio (OR) for each of five antigens using model 1 and model 2. The analysis also presents the calculated confidence interval (CI). A confidence interval that includes 1.0 indicates a correlation that is too ambiguous. Using model 1 the CI for Rv2626c was 0.2-0.8, which is not overly ambiguous, but using model 2 the CI was 0.2-1.4, which is too ambiguous. Unambiguous results could be obtained in most cases by dichotomizing results into simply "Low" and "High" where "High" signifies strong antibody response and "Low" does not. In the case of the 38 kDa antigen, however, it was necessary using model 2 to trichotomize the results into "Low," "Medium", and "High", where only "High" signifies strong antibody response for purposes of an assay according to this invention. Table 4 shows that the confidence interval for "Medium" results with the 38 kDa antigen was 0.2-1.6, which was ambiguous, but that the confidence interval for "High" results with the same antigen was 0.1-0.7, which was not ambiguous.

In the analysis presented in Table 4, an odds ratio greater than 1 for "High" results (where the "cut-off" point for a positive result is to be set to be greater than the upper limit of the "Low" range or, if trichotomized, greater than the upper limit of the "Medium" range) indicates results that are more likely to occur if the sample is from someone with inactive TB than if the sample is from someone with active TB. The higher the OR, the higher the odds or likelihood that that is the case. Conversely, an OR for "High" results that is less than 1.0 indicates results that are less likely to occur if the sample is from someone with inactive TB than from someone with active TB. This is the case, for example, with AlaDH. One can see from Table 3 that for AlaDH a positive result designed to be only in the "High" range by an appropriate cut-off also differentiates active TB from the CXR-normal classes. The analysis presented in Table 5 is similarly interpreted, although "High" results always indicate a sample more likely to have come from someone with inactive TB than from someone with a normal chest x-ray state (OR above 1.0 in all cases).

Comparing Table 4 with Table 5, it will be noted that two of the tested antigens, 16 kDa and ESAT-6, occur in both tables. For these antigens a "High" result indicates that the sample is more likely to be inactive TB rather than either active TB or a state (latent infection or infection-free) lacking radiographic abnormality.

It will be understood that high/low or high/medium/low are the categories for each antibody that reflect the LEVEL of response, that is, how much antibody is in serum. The OR ratio, greater or lower than 1, indicates the likelihood that a person with a particular antibody level is either active or inactive (Table 4) and either inactive or CXR-normal (Table 5). That is, first the antibody level categories are made, and then they are analyzed statistically for correlation with a TB state by estimating the odds ratio.

From Table 4, I have identified the several antigen combinations for assays according to this invention for distinguishing inactive TB from active TB. Using the model 1 analysis the combination is Rv2626c, 16 kDa and ESAT-6. Using the model 2 analysis, the combinations are three or more antigens from the group 16 kDa, ESAT-6, AlaDH and 38 kDa Ag, wherein at least one has an OR above 1.0 and at least one has an OR below 1.0. Examples include 16 kDa Ag, ESAT-6 and one or both of AlaDH and 38 kDa Ag; and AlaDH, 38 kDa Ag and one or both of 16 kDa Ag and ESAT-6. From Table 4 and Table 5, a preferred assay that includes differentiation of inactive TB from CXR-normal states as well would include antigens FdxA, ESAT-6, 16 kDa Ag and one or both of AlaDH and 38 kDa Ag, that is, either four or five antigens from the group tested. Antigen FdxA could be included as an additional antigen in any such combination. More preferred are assays that include at least two antigens to differentiate inactive TB from CXR-normal states, that is, at least two of 16 kDa Ag, ESAT-6 and FdxA.

EXPERIMENTAL WORK AND ANALYSIS

Materials and Methods

Study population. The study was conducted with stored serum samples obtained between 1995 and 1998 from immigrants referred to the Montreal Chest Institute, Montreal, Canada as TB suspects and from Canadian-born persons with pulmonary TB. Informed consent was obtained from patients; human experimentation guidelines of the US Department of Health and Human Services and/or those of the authors' institutions (Montreal Chest Institute Research Ethics Board and New York University Institutional Review Board) were followed in the conduct of this work.

Sera were collected from four groups: (i) active tuberculosis: 53 persons diagnosed as having active pulmonary TB, based on microbiological data and clinical evaluation (7 culture and smear positive, 31 culture positive and smear negative, and the remaining 15 negative to both tests). (ii) inactive tuberculosis: this category was defined by a positive response to the tuberculin skin test (TST) (>10 mm), abnormal but stable chest X ray (CXR) findings consistent with past TB, and the absence of clinical, bacteriological or radiographic evidence of current disease (1). Inactive TB was diagnosed in 218 persons, none of whom had a history of treated TB. (iii) TST positive: 32 subjects were positive to TST (>10 mm) and had a normal chest X ray, and (iv) TST negative: 50 study subjects were TST negative.

Antigens. Proteins of *M. tuberculosis* were selected either because they were known to elicit antibody responses, e.g., 38 kDa Ag (8), ESAT-6 (22), glutamine synthase (GluS) (9), alanine dehydrogenase (AlaDH) (11), superoxide dismutase A (SodA) (30), 16 kDa Ag (29), or because they were expected to be preferentially expressed in non-replicating bacilli. The antigen referred to herein as "16 kDa" is the product of gene rv2031c, and has sometimes been referred to in the literature as "14 kDa." The 16 kDa Ag (α-crystallin, Acr), ferredoxin A (FdxA) and Rv2626c are all encoded by genes found in the so-called dormancy (dosR) regulon (18, 25). *M. tuberculosis* proteins were expressed as recombinant products in *Escherichia coli* and purified to near-homogeneity by sequential column chromatography, as described (5). For clarity, it may be helpful to correlate the antigens with the genes that produce them. That correlation is: 16 kDa antigen, gene rv 2031c; ESAT-6, gene rv 3875; AlaDH, gene rv 2780; 38 kDa, gene rv 0934; FDXa, gene rv2007c.

Enzyme-linked immunosorbent assay (ELISA). Polystyrene 96-well microtiter plates (Bio-Rad Laboratories, Hercules, Calif., USA) were coated at 4° C. overnight with 2.0 µg/ml (0.2 ml/well) purified antigen in carbonate-bicarbonate buffer (pH 9.6). Plates were blocked with 1% non-fat skim milk in phosphate-buffered saline (pH 7.4) containing 0.05% Tween 20 (PBS-T) for 3 h at 37° C. and washed twice with PBS-T. Serum was diluted 1:50 in PBS-T containing 1% skim milk, and 0.2 ml of diluted serum was added to antigen-coated wells in duplicate and incubated for 30 min at 37° C. Positive and negative control sera were included in duplicate to control for inter- and intra-run variations. After washing with PBS-T, plates were incubated with 0.2 ml/well goat anti-human IgG conjugated with horseradish peroxidase (Dako, Glostrup, Denmark) diluted 1:20,000 in PBS-T plus 1% skim milk for 30 min at 37° C. Plates were washed with PBS-T, and enzyme activity was assayed by incubation for 30 min at room temperature with 0.2 ml/well TMB peroxidase substrate kit (Bio-Rad Laboratories, Hercules, Calif., USA). Reactions were stopped by adding 0.05 ml of 1N $H_2SO_4$. Optical density at 450 nm ($OD_{450}$) was measured with an automatic microplate reader (Spectra Shell, Tecan Systems Inc., San Jose, Calif., USA).

Serologic data analysis. Chi-square tests were used to assess associations between demographic and diagnostic categories. Comparisons of antibody responses by tuberculosis state were conducted using non-parametric tests, such as the Wilcoxon rank sum test for two independent variables and the Kruskal-Wallis test for three or more independent variables.

A logistic regression model was estimated separately for active TB vs. inactive TB cases and for CXR-normal (i.e., subjects who had no radiographic signs of active or inactive TB) vs. inactive TB cases via backward elimination from a full model containing antibody responses identified as statistically significant by the analysis described in the previous paragraph, adjusting for BCG vaccination and world region of origin. Antibody results were dichotomized into categories "low and high" according to being higher or lower than the median, or trichotomized into "low, medium and high" according to the tertiles of the antibody distribution. The initial modeling approach utilized a trichotomous parameterization of the antibodies; when differences in risk between two contiguous antibody categories were small, a dichotomous parameterization was selected.

Results

Characteristics of the study population. The 353 subjects included in the study were divided in four categories—active TB, inactive TB, latent *M. tuberculosis* infection (TST positive), and free of *M. tuberculosis* infection (TST negative)—(Table 1). The demographic characteristics of the study population are described in Table 2. No statistically significant difference was found by chi-square test among the four diagnostic categories for factors associated with tuberculosis risk (1), such as age group (p=0.29), gender (p=0.07), country of origin (p=0.12), status of vaccination with *M. bovis* BCG (p=0.19), or years in Canada (less than 1, greater than 1; p=0.53).

Distribution of antibody levels. Serum levels of specific IgG antibodies were measured by ELISA and expressed as $OD_{450}$. Only the Rv2626c antibody was approximately normal after log-transformation (data not shown). Therefore, ELISA measurements of serum antibody levels for all 353 subjects are presented as median and range (minimum and maximum) (Table 3).

Comparisons of antibody distributions were conducted by non-parametric statistical methods, such as the Wilcoxon rank sum test and the Kruskal-Wallis test, rather than by one-way ANOVA, which requires an assumption of normality. No statistically significant difference was found between the TST positive and the TST negative groups for any of the antibodies considered (p>0.50 for all) (data not shown). This result agrees with the notion that latent infection per se fails to provide sufficient antigenic stimulus to elicit a strong antibody response (3, 12, 24). Thus, these two categories were combined for subsequent analysis into a single, radiographically normal group ("CXR-normal"), regardless of *M. tuberculosis* infection.

Antibody responses were analyzed by state, i.e., active TB, inactive TB, and CXR-normal; differences among the states were found to be statistically significant at p<0.05 for all antibodies. The finding that the inactive TB and CXR-normal groups were serologically distinguishable strongly implies that persons having inactive tuberculosis are more likely to bear a higher antigen burden than those having latent infection without CXR abnormalities. This interpretation is consistent with the greater risk of disease reactivation associated with inactive TB than with latent infection with normal CXR (6, 7, 16).

In post-hoc comparisons, statistical significance was declared at an alpha of 0.003, thereby controlling for multiple comparisons with the Bonferroni approach (8 antigens and 2 comparisons between disease states implies alpha=0.003≈0.05/[8×2]). Inactive tuberculosis was arbitrarily taken as the reference state for this analysis (Table 3). Antibodies to AlaDH, 38 kDa Ag, ESAT-6 and 16 kDa Ag distinguished inactive TB from both active TB and CXR-normal state. The antibody to Rv2626c distinguished inactive TB from active TB, while the antibody to FdxA distinguished inactive TB from the CXR-normal state. No difference was found in the levels of antibodies to SodA and to GluS in the three states (data not shown). Thus these two antibodies were excluded from further analyses.

Logistic regression results. Since antibody profiles differed among the three TB states (active TB, inactive TB, and CXR-normal), logistic regression models were estimated in order to predict TB state as a function of the antibodies identified as statistically significant in the analysis presented in Table 3. Backward elimination was used for all models. Two models of inactive TB vs. active TB were estimated: model 1 was based on antibodies identified as being statistically significant at alpha=0.003, and model 2 was based on antibodies identified as statistically significant at alpha=0.05 (Table 4). According to model 1, high levels of antibodies to 16 kDa Ag and ESAT-6 and low levels of antibodies to Rv2626c increased the odds of inactive TB compared with active TB. Model 2 additionally indicated that low levels of antibodies to AlaDH and 38 kDa Ag increased the odds of inactive TB over active TB. With the latter model, the contribution of the antibody to Rv2626c lost statistical significance.

Only one model was estimated for inactive TB vs. CXR-normal (model 3), because for that comparison all antibodies were statistically significant both at alpha=0.003 and at alpha=0.05 (Table 5). According to model 3, high levels of antibodies to 16 kDa Ag, ESAT-6 and FdxA increased the odds of inactive TB vs. CXR-normal. A trend of increasing odds was detected in the three categories of antibody level, further strengthening the results of this comparison.

Antibody profiles associated with inactive TB differed from those associated with active TB, strongly suggesting that the targets of the antibody response during latent infection differ from those occurring during active disease. These data show that, in humans, each tuberculosis state is characterized by bacterial antigen signatures. These signatures resemble "bar-codes", i.e., particular combinations of presence and absence of antigen-specific markers. The bar-code idea reveals a flaw in current strategies of TB immunodiagnostics development, which have been based solely on identifying markers positively associated with a particular state.

Other aspects of the antibody profiles generated in the study are less straightforward. The antibody profiles to the 16 kDa Ag, FdxA, and Rv2626c are specific for different tuberculosis states. However, these three antigens are encoded by genes (acr, fdxA and rv2626c) that are members of the same "dormancy" regulon (18, 25). Different antibody profiles to these antigens are therefore suggestive of differential regulation of these bacterial genes in humans or of differences in relative immunodominance, antibody affinity, or immune regulation. For example, unlike FdxA and the 16 kDa Ag, Rv2626c may not achieve threshold levels for antibody production in inactive TB, thus becoming detectable only in active TB, which is associated with a higher bacterial burden. More intriguingly, the detection of antibodies to FdxA and Rv2626c in active TB indicates sufficient antigenic stimulus, suggesting that the concurrent lack of antibody responses to the 16 kDa Ag is likely due either to a selective down-regulation of acr in particular human host microenvironments, or to a failure of this antigen to elicit antibody production in forms of disease characterized by tubercle bacilli growing at low multiplicity [most active TB cases in the present study had smear-negative, pulmonary disease]. A similar interpretation can be given to the data on the anti-ESAT-6 antibody, which strongly correlates with inactive TB. Indeed, the anti-16 kDa-Ag and anti-ESAT-6 antibodies correlate with each other (data not shown).

The present study has some limitations. One lies in the composition of the serum bank, which was characterized by highly diverse demographics and by a vast predominance of inactive TB cases. Another is that the current analysis was limited to only eight antibody profiles. However, statistically filtering the serological data with the Kruskal-Wallis test to select antibodies for use in subsequent logistic regression models utilizes a strategy that may be employed with very large numbers of antibodies, such as those that might be detected by use of *M. tuberculosis* protein microarrays. Moreover, correlations between antibody profiles and tuberculosis state measured in the present study will have to be validated in independent populations.

The identification of immune profiles characteristic of tuberculosis state suggests that progression from latent *M. tuberculosis* infection to active disease, which is presumably accompanied by resumed bacterial multiplication, may also be accompanied by changes of bacterial antigen composition. Thus, asymptomatic, infected individuals that are progressing to reactivation disease may be serologically distinguishable from those that are not. Identification of "progressors" through immunological screens should greatly help target the treatment of latent tuberculosis.

REFERENCES

1. American Thoracic Society. 2000. Diagnostic Standards and Classification of Tuberculosis in Adults and Children. Am J Respir Crit Care Med 161:1376-95.
2. Bifani, P. J., B. Mathema, N. E. Kurepina, and B. N. Kreiswirth. 2002. Global dissemination of the *Mycobacterium tuberculosis* W-Beijing family strains. Trends Microbiol 10:45-52.
3. Bothamley, G. H. 1995. Serological diagnosis of tuberculosis. Eur. Respir. J. 8, suppl. 20:676s-688s.
4. Bothamley, G. H., J. S. Beck, R. C. Potts, J. M. Grange, T. Kardjito, and J. Ivanyi. 1992. Specificity of antibodies and tuberculin response after occupational exposure to tuberculosis. J Infect Dis 166:182-6.
5. Colangeli, R., A. Heijbel, A. Williams, C. Manca, J. Chan, K. Lyashchenko, and M. L. Gennaro. 1998. Three-step purification of lipopolysaccharide-free, polyhistidine-tagged recombinant antigens of *Mycobacterium tuberculosis*. J. Chromatogr. B 714:223-235.
6. Grzybowksi, S., N. McKinnon, L. Tuters, G. Pinkus, and R. Philipps. 1966. Reactivation in inactive pulmonary tuberculosis. Am Rev Resp Dis 93:352-360.
7. Grzybowski, S., H. Fishaut, J. Rowe, and A. Brown. 1971. Tuberculosis among patients with various radiologic abnormalities, followed by the chest clinic service. Am Rev Resp Dis 104:605-608.
8. Harboe, M., and H. G. Wiker. 1992. The 38-kDa protein of *Mycobacterium tuberculosis*: a review. J. Infect. Dis. 166:874-884.
9. Harth, G., D. L. Clemens, and M. A. Horwitz. 1994. Glutamine synthetase of *Mycobacterium tuberculosis*: extracellular release and characterization of its enzymatic activity. Proc Natl Acad Sci USA 91:9342-6.
10. Honer zu Bentrup, K., and D. G. Russell. 2001. Mycobacterial persistence: adaptation to a changing environment. Trends Microbiol 9:597-605.
11. Hutter, B., and M. Singh. 1999. Properties of the 40 kDa antigen of *Mycobacterium tuberculosis*, a functional L-alanine dehydrogenase. Biochem J 343 Pt 3:669-72.
12. Kaplan, M. H., and M. W. Chase. 1980. Antibodies to mycobacteria in human tuberculosis. I. Development of antibodies before and after antimicrobial therapy. J Infect Dis 142:825-34.
13. Manca, C., L. Tsenova, C. E. Barry, 3rd, A. Bergtold, S. Freeman, P. A. Haslett, J. M. Musser, V. H. Freedman, and G. Kaplan. 1999. *Mycobacterium tuberculosis* CDC1551 induces a more vigorous host response in vivo and in vitro, but is not more virulent than other clinical isolates. J Immunol 162:6740-6.
14. McKinney, J. D., K. Honer zu Bentrup, E. J. Munoz-Elias, A. Miczak, B. Chen, W. T. Chan, D. Swenson, J. C. Sacchettini, W. R. Jacobs, Jr., and D. G. Russell. 2000. Persistence of *Mycobacterium tuberculosis* in macrophages and mice requires the glyoxylate shunt enzyme isocitrate lyase. Nature 406:735-8.
15. Monack, D. M., A. Mueller, and S. Falkow. 2004. Persistent bacterial infections: the interface of the pathogen and the host immune system. Nat Rev Microbiol 2:747-65.
16. Nolan, C., and E. AM. 1988. Tuberculosis in a cohort of Southeast Asian refugees. Am Rev Resp Dis 137:805-809.
17. Segal, W. 1984. Growth dynamics of in vivo and in vitro grown mycobacterial pathogens, p. 547-573. In G. P. Kubica and L. G. Wayne (ed.), The Mycobacteria. A sourcebook. Marcel Dekker, Inc., New York.
18. Sherman, D. R., M. Voskuil, D. Schnappinger, R. Liao, M. I. Harrell, and G. K. Schoolnik. 2001. Regulation of the *Mycobacterium tuberculosis* hypoxic response gene encoding alpha-crystallin. Proc Natl Acad Sci USA 98:7534-9.
19. Shi, L., Y. J. Jung, S. Tyagi, M. L. Gennaro, and R. J. North. 2003. Expression of Th1-mediated immunity in mouse lungs induces a *Mycobacterium tuberculosis* transcription pattern characteristic of nonreplicating persistence. Proc Natl Acad Sci USA 100:241-6.
20. Shi, L., R. North, and M. Gennaro. 2004. Effect of growth state on transcription levels of genes encoding major secreted antigens of *Mycobacterium tuberculosis* in mouse lung. Infect. Immun. 72:2420-2424.
21. Silva, V. M. C., G. Kanaujia, M. L. Gennaro, and D. Menzies. 2003. Factors associated with humoral response to ESAT-6, 38 kDa and 14 kDa antigens in patients with a spectrum of tuberculosis. Int. J. Tub. Lung Dis 7:478-484.
22. Sorensen, A. L., S. Nagai, G. Houen, P. Andersen, and A. B. Andersen. 1995. Purification and characterization of a low-molecular-mass T-cell antigen secreted by *Mycobacterium tuberculosis*. Infect. Immun. 63:1710-1717.
23. Stewart, G. R., B. D. Robertson, and D. B. Young. 2003. Tuberculosis: a problem with persistence. Nat Rev Microbiol 1:97-105.

24. Turneer, M., J. P. Van Vooren, J. De Bruyn, E. Serruys, P. Dierckx, and J. C. Yernault. 1988. Humoral immune response in human tuberculosis: immunoglobulins G, A, and M directed against the purified P32 protein antigen of *Mycobacterium bovis bacillus Calmette-Guerin*. J Clin Microbiol 26:1714-9.
25. Voskuil, M. I., D. Schnappinger, K. C. Visconti, M. I. Harrell, G. M. Dolganov, D. R. Sherman, and G. K. Schoolnik. 2003. Inhibition of respiration by nitric oxide induces a *Mycobacterium tuberculosis* dormancy program. J Exp Med 198:705-13.
26. Wayne, L. G. 1994. Dormancy of *Mycobacterium tuberculosis* and latency of disease. Eur J Clin Microbiol Infect Dis 13:908-14.
27. Weber, I., C. Fritz, S. Ruttkowski, A. Kreft, and F. C. Bange. 2000. Anaerobic nitrate reductase (narGHJI) activity of *Mycobacterium bovis* BCG in vitro and its contribution to virulence in immunodeficient mice. Mol Microbiol 35:1017-25.
28. Wilkins, E. G. L. 1994. The serodiagnosis of tuberculosis, p. 367-380. In P. D. O. Davies (ed.), Clinical tuberculosis. Chapman and Hall Medical, London.
29. Wilkinson, R. J., K. A. Wilkinson, K. A. De Smet, K. Haslov, G. Pasvol, M. Singh, I. Svarcova, and J. Ivanyi. 1998. Human T- and B-cell reactivity to the 16 kDa alpha-crystallin protein of *Mycobacterium tuberculosis*. Scand J Immunol 48:403-9.
30. Zhang, Y., R. Lathigra, T. Garbe, D. Catty, and D. Young. 1991. Genetic analysis of superoxide dismutase, the 23 kilodalton antigen of *Mycobacterium tuberculosis*. Mol. Microbiol. 5:381-391.
31. Zuber, P., M. McKenna, N. Binkin, I. Onorato, and K. Castro. 1997. Long-term risk of tuberculosis among foreign-born persons in the United States. JAMA 278:304-307.

TABLE 1

Diagnosis with respect to TB state.

| Diagnosis | Frequency | Percent |
|---|---|---|
| Active TB | 53 | 15.0 |
| Inactive TB | 218 | 61.8 |
| TST positive | 32 | 9.1 |
| TST negative | 50 | 14.2 |
| Total | 353 | 100.0 |

Diagnostic definitions are provided in Materials and Methods. TB, tuberculosis; TST, tuberculin skin test.

Diagnostic definitions are provided in Materials and Methods. TB, Tuberculosis; TST, tuberculin skin test.

TABLE 2

Demographics

| Category | Frequency | Percent |
|---|---|---|
| Age | | |
| 25 and under | 29 | 8.2 |
| 25 to 34 yrs | 106 | 30.0 |
| 35-44 | 88 | 24.9 |
| 45 to 54 | 40 | 11.3 |
| 55 and higher | 90 | 25.5 |
| Gender | | |
| Female | 126 | 35.7 |
| Male | 227 | 64.3 |

TABLE 2-continued

Demographics

| Category | Frequency | Percent |
|---|---|---|
| World region of birth | | |
| Canada and Western Europe | 31 | 8.8 |
| Eastern Europe | 30 | 8.5 |
| Africa and Middle East | 67 | 19.0 |
| South Asia | 83 | 23.5 |
| South-East Asia | 62 | 17.6 |
| Caribbean and Latin America | 80 | 22.7 |
| Years in Canada* | | |
| Less than 1 yr | 233 | 66.0 |
| More than 1 yr | 76 | 21.5 |
| n.a. or unknown | 44 | 12.5 |
| BCG vaccination | | |
| No | 169 | 47.9 |
| Unknown | 76 | 21.5 |
| Yes | 108 | 30.6 |
| Total | 353 | 100.0 |

*A one-year mark was selected because there is substantial evidence that a large proportion of TB among immigrants occurs soon after arrival in the new country (31).

TABLE 3

Unadjusted median antibody responses by disease state.

| | | | Range | | |
|---|---|---|---|---|---|
| Antigen | Disease state | Median | min | max | p-value |
| Rv2626c | Active | 0.245 | 0.09 | 1.09 | <0.001** |
| | Inactive | 0.178 | 0.02 | 1.38 | n.a. |
| | CXR-normal | 0.185 | 0.02 | 1.15 | 0.356 |
| FdxA | Active | 0.176 | 0.06 | 1.76 | 0.284 |
| | Inactive | 0.164 | 0.01 | 1.95 | n.a. |
| | CXR-normal | 0.107 | 0.02 | 0.81 | <0.001** |
| AlaDH | Active | 0.199 | 0.07 | 1.23 | 0.005* |
| | Inactive | 0.140 | 0.01 | 3.56 | n.a. |
| | CXR-normal | 0.106 | 0.01 | 1.08 | 0.001** |
| 38 kDa Ag | Active | 0.510 | 0.01 | 3.90 | 0.020* |
| | Inactive | 0.260 | 0.01 | 3.99 | n.a. |
| | CXR-normal | 0.155 | 0.01 | 2.01 | 0.002** |
| ESAT-6 | Active | 0.090 | 0.01 | 3.86 | <0.001** |
| | Inactive | 0.210 | 0.02 | 3.98 | n.a. |
| | CXR-normal | 0.065 | 0.01 | 2.26 | <0.001** |
| 16 kDa Ag | Active | 0.050 | 0.01 | 3.81 | <0.001** |
| | Inactive | 0.140 | 0.01 | 3.60 | n.a. |
| | CXR-normal | 0.050 | 0.01 | 0.58 | <0.001** |

Values of median and range (minimum and maximum) are shown since the antibody distributions were not normally distributed. p-values comparing active TB to inactive TB, and CXR-normal to inactive TB were based on the Kruskal-Wallis test. n.a., not applicable.
*denotes differences that are statistically significant at alpha = 0.05.
**denotes differences that are statistically significant at alpha = 0.003. Alpha was selected according to the Bonferroni criterion, since the analysis included eight antibodies and two comparisons: inactive vs. active and inactive vs. CXR-normal [0.003 ≈ 0.05/(2 × 8)].

TABLE 4

Models of inactive TB vs. active TB, adjusted for BCG vaccination status and place of birth.

| Antibody to | Category | Range | OR [CI]: Model 1 | OR [CI]: Model 2 |
|---|---|---|---|---|
| 16 kDa Ag | Low | ≤0.11 | 1.0 (Ref.) | 1.0 (Ref.) |
| | High | 0.12-3.81 | 5.5 [2.4, 12.5] | 7.3 [3.0, 17.9] |
| Rv2626c | Low | ≤0.19 | 1.0 (Ref.) | 1.0 (Ref.) |
| | High | 0.19-1.38 | 0.4 [0.2, 0.8] | 0.6 [0.2, 1.4] |
| ESAT-6 | Low | ≤0.15 | 1.0 (Ref.) | 1.0 (Ref.) |
| | High | 0.15, 3.98 | 3.0 [1.4, 6.6] | 2.7 [1.2, 6.1] |
| AlaDH | Low | ≤0.15 | n.a. | 1.0 (Ref.) |
| | High | 0.15-3.56 | n.a. | 0.3 [0.1, 0.7] |

TABLE 4-continued

Models of inactive TB vs. active TB, adjusted
for BCG vaccination status and place of birth.

| Antibody to | Category | Range | OR [CI]: Model 1 | OR [CI]: Model 2 |
|---|---|---|---|---|
| 38 kDa Ag | Low | ≦0.14 | n.a. | 1.0 (Ref.) |
|  | Medium | 0.14-0.49 | n.a. | 0.6 [0.2, 1.6] |
|  | High | 0.50-3.99 | n.a. | 0.3 [0.1, 0.7] |

ELISA results were dichotomized into categories "low and high" according to being higher or lower than the median, or trichotomized into "low, medium and high" according to the textiles of the antibody distribution.
Model 1 is based on a backward elimination from a model using only antibodies significant at alpha = 0.003 in Table 3; model 2 is derived from a backward elimination from a model using antibodies significant at alpha = 0.05 in Table 3.
OR, odds ratio; CI, confidence interval; Ref., reference range; n.a., not applicable.

ELISA results were dichotomized into categories "low and high" according to being higher or lower than the median, or trichotomized into "low, medium and high " according to the textiles of the antibody distribution.

Model 1 is based on a backward elimination from a model using only antibodies significant from a model using antibodies significant at alpha=0.05 in Table 3.

OR, odds ratio; CI, confidence interval; Ref., reference range; n.a., not applicable.

TABLE 5

Models of inactive TB vs. CXR-normal, adjusted
for BCG vaccination status and place of birth.

| Antibody to | Category | Range | OR [CI]: Model 3 | Test for trend |
|---|---|---|---|---|
| 16 kDa Ag | Low | ≦0.06 | 1.0 (Ref.) |  |
|  | Medium | 0.07, 0.14 | 4.0 [1.9, 8.5] | P < 0.001 |
|  | High | 0.15, 3.60 | 11.7 [4.9, 34.0] |  |
| ESAT-6 | Low | ≦0.09 | 1.0 (Ref.) |  |
|  | Medium | 0.09-0.2 | 1.9 [0.8, 4.1] | P = 0.001 |
|  | High | 0.2-4.0 | 5.9 [2.0, 17.6] |  |
| FdxA | Low | ≦0.11 | 1.0 (Ref.) |  |
|  | Medium | 0.11-0.19 | 1.5 [0.7, 3.2] | P = 0.016 |
|  | High | 0.19-1.95 | 2.8 [1.2, 6.4] |  |

ELISA results were trichotomized into the categories "low, medium and high" according to the tertiles of the overall antibody distribution. Model 3 based on backward elimination from antibodies found to be significant at alpha=0.003 in Table 3.

Based on the foregoing analysis, an evaluation was performed to compare the results of performing the ELISA described above with single antigens or the panel of eight antigens tested. A subject's model-based predictions were obtained by substituting the subject's antibody values into the estimated logistic regression model and by solving for the probability of the outcome of interest, that is, the probability of being diagnosed with inactive TB. If this probability exceeds 50%, then the prediction of inactive TB is made; otherwise, the prediction is the alternate diagnosis.

"Active TB only" indicates the percent of subjects with active TB who are correctly predicted to have active TB, and "CXR-normal only" is the percent of subjects with CXR-normal who are correctly predicted to have a CXR-normal class. Results are presented in Table 6.

TABLE 6

Concordance between predictions and observations.

| Model | Concordance, % Active TB only | Model | Concordance, % CXR-normal only |
|---|---|---|---|
| Model 1 | 35.8 | Model 3 | 57.3 |
| Model 2 | 43.4 | FdxA only | 9.8 |
| Rv2626c only | 5.7 | ESAT-6 only | 58.5 |
| ESAT-6 only | 11.3 | 14 kDa Ag only | 62.2 |
| 14 kDa Ag only | 15.1 | only |  |
| AlaDH only | 13.2 |  |  |
| 38 kDa Ag only | 11.3 |  |  |

Referring to the right side of Table 6 it will be seen that the chosen panel did not do better than the individual antigens ESAT-6 or 16 kDa, even though the panel contained both. The reason is that antibodies against these antigens tend to go together. Accordingly, combining two antigens whose binding correlates with inactive TB gave little improvement. Referring to the left side of Table 6, it will be seen that the chosen panel did much better than any individual antigen in identifying active cases.

A number of embodiments of the invention have been described. Nevertheless, it will be understood that various modifications may be made without departing from the spirit and scope of the invention. For example, different antigen combinations can be used, as well as different antibody assays. Accordingly, other embodiments are within the scope of the following claims.

What is claimed is:

1. An assay for tuberculosis that is performed on a serum sample from a human subject, wherein the assay is capable of determining the likelihood that the subject has active tuberculosis or inactive tuberculosis, the assay comprising exposing antibodies in the sample to at least three different *M. tuberculosis* protein antigens separately immobilized on different locations on a surface, wherein the at least three different *M. tuberculosis* protein antigens include at least one antigen of a first type selected from the group consisting of 16 kDa antigen (product of gene rv 2031c) and ESAT-6 antigen (product of gene rv 3875), at least one antigen of a second type selected from the group consisting of Rv2626c antigen, AlaDH antigen (product of gene rv 2780) and 38 kDa antigen (product of gene rv 0934), and at least one antigen of a third type selected from the group consisting of 16 kDa antigen (product of gene rv 2031c), ESAT-6 antigen (product of gene rv 3875), Rv2626c antigen, AlaDH antigen (product of gene rv 2780) and 38 kDa antigen (product of gene rv 0934), and detecting serum antibodies to said antigens.

2. The assay according to claim 1 that includes at least 16 kDa antigen and ESAT-6 antigen and at least two antigens of the second type.

3. The assay of claim 1 that includes at least 16 kDa antigen and ESAT-6 antigen, further comprising FdxA antigen (product of gene rv 2007c).

4. A kit of reagents for performing a tuberculosis assay that is capable of determining the likelihood that a subject has active tuberculosis or inactive tuberculosis, said kit comprising at least three different *M. tuberculosis* protein antigens separately immobilized on different locations on a surface, wherein the at least three different *M. tuberculosis* protein antigens include at least one antigen of a first type selected from the group consisting of 16 kDa antigen (product of gene rv 2031c) and ESAT-6 antigen (product of gene rv 3875), at least one antigen of a second type selected from the group consisting of Rv2626c antigen, AlaDH antigen (product of gene rv 2780) and 38 kDa antigen (product of gene rv 0934), and at least one antigen of a third type selected from the group consisting of Rv2626c antigen, AlaDH antigen (product of gene rv 2780) and FdxA antigen (product of gene rv 2007c), and reagents for detecting binding of antibodies to said antigens.

5. The kit according to claim 4 that includes at least 16 kDa antigen and ESAT-6 antigen and at least two antigens of the second type.

6. The kit according to claim 4 that includes at least 16 kDa antigen, ESAT-6 antigen, and FdxA antigen (product of gene rv 2007c).

* * * * *